US007582312B2

(12) United States Patent
Johnson et al.

(10) Patent No.: US 7,582,312 B2
(45) Date of Patent: Sep. 1, 2009

(54) METHODS TO PRODUCE LUNG SURFACTANT FORMULATIONS VIA LYOPHILIZATION AND FORMULATIONS AND USES THEREOF

(75) Inventors: Mark Johnson, Los Altos, CA (US); Roy Coe, Bordentown, NJ (US)

(73) Assignee: Discovery Laboratories, Inc., Warrington, PA (US)

( * ) Notice: Subject to any disclaimer, the term of this patent is extended or adjusted under 35 U.S.C. 154(b) by 0 days.

(21) Appl. No.: 11/274,701

(22) Filed: Nov. 14, 2005

(65) Prior Publication Data
US 2006/0205663 A1    Sep. 14, 2006

Related U.S. Application Data

(60) Provisional application No. 60/628,365, filed on Nov. 15, 2004.

(51) Int. Cl.
| | | |
|---|---|---|
| C07C 7/00 | (2006.01) | |
| C07C 7/10 | (2006.01) | |
| A61K 9/00 | (2006.01) | |
| A61K 35/42 | (2006.01) | |
| A01N 37/18 | (2006.01) | |
| A61K 38/00 | (2006.01) | |

(52) U.S. Cl. ............... 424/499; 585/833; 585/864; 585/866; 585/867; 585/800; 424/400; 424/557; 424/489; 424/502; 514/2; 514/17; 514/15; 514/16; 514/18

(58) Field of Classification Search ............ None
See application file for complete search history.

(56) References Cited

U.S. PATENT DOCUMENTS

| | | | |
|---|---|---|---|
| 4,338,301 A | 7/1982 | Tetsuro et al. | 424/557 |
| 4,861,756 A | 8/1989 | Jackson | 514/11 |
| 4,916,220 A | 4/1990 | Galzigna et al. | 536/117 |
| 4,918,161 A | 4/1990 | Steinbrink | 530/300 |
| 5,006,343 A | 4/1991 | Benson et al. | 424/450 |
| 5,164,369 A | 11/1992 | Cochrane et al. | 514/12 |
| 5,223,481 A | 6/1993 | Curstedt et al. | 514/12 |
| 5,238,920 A | 8/1993 | Sarin et al. | 514/12 |
| 5,260,273 A | 11/1993 | Cochrane et al. | 514/12 |
| 5,272,252 A | 12/1993 | McLean et al. | 530/327 |
| 5,302,481 A | 4/1994 | Ong | 430/108.24 |
| 5,407,914 A | 4/1995 | Cochrane et al. | 514/12 |
| 5,455,227 A | 10/1995 | Curstedt et al. | 514/14 |
| 5,731,291 A | 3/1998 | Sullivan et al. | 514/23 |
| 5,741,523 A | 4/1998 | Teagarden et al. | 424/489 |
| 5,750,330 A | 5/1998 | Tometsko et al. | 435/2 |
| 5,753,621 A | 5/1998 | Dhaon et al. | 514/12 |
| 5,770,230 A | 6/1998 | Teagarden et al. | 424/489 |
| 5,789,381 A | 8/1998 | Cochrane et al. | 514/13 |
| 5,827,825 A | 10/1998 | Takei et al. | 514/12 |
| 5,840,527 A | 11/1998 | Schilling, Jr. et al. | 435/69.1 |
| 5,874,406 A | 2/1999 | Schafer et al. | 514/12 |
| 5,891,844 A | 4/1999 | Hafner | 514/7 |
| 5,952,303 A | 9/1999 | Bornstein et al. | 514/13 |
| 6,022,955 A | 2/2000 | Sarin et al. | 530/410 |
| 6,287,590 B1 * | 9/2001 | Dasseux | 424/450 |
| 6,451,990 B1 | 9/2002 | Bayod Jasanada et al. | 536/7.4 |
| 6,482,864 B1 | 11/2002 | Yamagata et al. | 514/772.4 |
| 6,613,734 B2 | 9/2003 | Cochrane et al. | 514/2 |
| 6,660,833 B1 | 12/2003 | Walther et al. | 530/324 |
| 2002/0164372 A1 | 11/2002 | Pestka | 424/469 |
| 2003/0017169 A1 | 1/2003 | Pestka | 424/185.1 |
| 2003/0099696 A1 | 5/2003 | Cochrane | 424/450 |
| 2004/0092587 A1 | 5/2004 | Takada et al. | 514/540 |
| 2005/0020615 A1 | 1/2005 | Rubino | 514/291 |

FOREIGN PATENT DOCUMENTS

| | | |
|---|---|---|
| EP | 0 119 056 B1 | 8/1990 |
| EP | 0 286 011 B1 | 1/1994 |
| EP | 0 725 642 B1 | 8/1996 |
| EP | 1 061 948 B1 | 12/2000 |
| EP | 0 733 645 B1 | 3/2003 |
| JP | 63270623 A | 11/1988 |
| JP | 7076515 A | 3/1995 |
| JP | 7165783 A | 6/1995 |
| JP | 2001039879 A | 2/2001 |
| WO | 86/03408 A1 | 6/1986 |
| WO | 89/04326 A1 | 5/1989 |
| WO | WO 00/76535 | 12/2000 |
| WO | WO 2005/055994 A | 6/2005 |

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Gennaro, A.R., "Filtrazation" in Remington's Pharmaceutical Sciences, 16th and 18th Eds., Mack Publishing Co., Easton, Pa. (1980 and 1990), p. 1474-1476).*
Bhattacharjya et al., Protein Sci. 1998 7: 123-131.*
Erdag et al., Cryobiology 2002, 44(3):218-228.*
U.S. Appl. No. 11/130,783, filed May 17, 2005, Niven.
Hopp, T. P. et al., "Prediction of protein antigenic determinants from amino acid sequences," Proc. Natl. Acad. Sci. 78(6), 3824-3829, 1981.
Glasser, S. W. et al., "cDNA and deduced amino acid sequence of human pulmonary surfactant-associated proteolipid SPL(Phe)," Proc. Natl. Acad. Sci. 84(12), 4007-4001, 1987.
Gennaro, A.R., "Filtration," In Remington's Pharmaceutical Sciences, 16th and 18th Eds., Mack Publishing Co., Easton, PA, 1980 and 1990, pp. 1474-1476.
Ngo, T. et al., "Computational Complexity, Protein Structure Prediction, and the Levinthal Paradox," In The Protein Folding Problem and Tertiary Structure Prediction, 1994, Merz et al. (ed.), Birkhauser, Boston, MA, pp. 433 and 492-495.

* cited by examiner

Primary Examiner—Rebecca E Prouty
Assistant Examiner—Jae W Lee
(74) Attorney, Agent, or Firm—Potter Anderson & Corroon LLP

(57) ABSTRACT

Methods of producing lung surfactant formulations through solvent dissolution and lyophilization are described as well as surfactant formulations derived therefrom. Methods of treating respiratory distress dysfunction are also provided.

13 Claims, 2 Drawing Sheets

METHODS TO PRODUCE LUNG SURFACTANT FORMULATIONS VIA LYOPHILIZATION AND FORMULATIONS AND USES THEREOF

CROSS-REFERENCE TO RELATED APPLICATIONS

This application claims priority, under 35 USC § 119(e), to U.S. Application No. 60/628,365, filed Nov. 15, 2004, the disclosure of which is incorporated by reference in its entirety.

FIELD

The invention is directed to methods of producing lung surfactant formulations via solvent dissolution and lyophilization. The invention is also directed to surfactant formulations derived therefrom and methods of treating respiratory distress dysfunction.

BACKGROUND

Pulmonary surfactant (also referred to as "lung surfactant") is a complex mixture of lipids and proteins that promote the formation of a monolayer at the alveolar air-water interface, and by reducing the surface tension, prevents the collapse of the alveolus during expiration. Lung surfactant lines the alveolar epithelium of mature mammalian lungs. Natural lung surfactant has been described as a "lipoprotein complex" because it contains both phospholipids and apoproteins that interact to reduce surface tension at the lung air-liquid interface. Four proteins have been found to be associated with lung surfactant, namely SP-A, SP-B, SP-C, and SP-D. Specifically, SP-B appears to be essential for the biophysical action of lung surfactant. It is accepted therapy for the treatment of a variety of respiratory disorders to administer lung surfactant to the patient's lungs.

From a pharmacological point of view, the optimal exogenous lung surfactant to use in the treatment would be completely synthesized in the laboratory. In this regard, one mimetic or mimic of SP-B that has found to be useful is KL4, which is a 21 amino acid cationic polypeptide.

One method of manufacturing lung surfactant on a commercial-scale for medical use is by a process that utilizes a thin film evaporator (TFE) unit operation. The process as it applies to the production of KL4 lung surfactant consists of the following steps: 1) solubilizing the four primary formulation components, dipalmitoyl phosphatidylcholine (DPPC), palmitoyloleoyl phosphatidylglycerol (POPG) and palmitic acid (PA) and KL4 in ethanol; 2) removing the ethanol utilizing the TFE; and 3) vialing the final dispersion. The TFE unit operation itself is complex and has scaling limitations. Specifically, a 1 ft$^2$ TFE produces a 40-liter batch and the biggest comparable unit available is a 10 ft$^2$ TFE. This restricts the batch size which is undesirable as additional indications are approved for the KL4 surfactant requiring ever increasing amounts of surfactant. Moreover, the process is performed under aseptic conditions that contribute significantly to the cost, scheduling flexibility, and complexity of the product.

In addition to the cost and complexity of using a TFE, a further complication exists due to the composition being stored in a liquid state. Because the polypeptide and lipid components of the composition are subject to degradation, the solution must be kept refrigerated to retard any degradation and achieve long term stability.

It is well known in the art that lyophilizing products, such as injectable pharmaceuticals, which are relatively unstable in aqueous solution can result in solid phase products that are more stabile and therefore have a longer shelf life. Examples of pharmaceuticals that are lyophilized include alprostadil, alplidine, beta-interferon, amoxicillin sodium, tobramycin sulfate, gentamicin sulfate, cardiotonic phosphodiesterase inhibitors, cyclohexane-1,2-diaminePt(II) complex, annamycin, fructose-1,6-diphosphate, and the like.

In order to provide a KL4 pulmonary surfactant with improved stability at room temperature, attempts have been made to lyophilize the surfactant composition as described in U.S. Pat. No. 5,952,303. However, there is a need for improved methods of producing lung surfactant compositions and improved lung surfactant compositions. The present invention is directed to this and other important ends.

SUMMARY

The present inventors have discovered that a surfactant composition can be prepared by lyophilization from an organic solvent. Without being limited to any one theory, it is believed that the organic solvent interacts with and more thoroughly solubilizes the components of the pulmonary surfactant thereby providing a more intimate admixture. In certain embodiments, the lyophilized surfactant compositions, when reconstituted or rehydrated, have reduced viscosity relative to the pre-lyophilized state and reduced surface tension relative to the pre-lyophilized state. In certain embodiments, the lyophilized surfactant compositions have improved stability when stored at room temperature relative to the pre-lyophilized state and the lyophilized surfactant readily reconstitutes to a well-dispersed colloidal state upon addition of an aqueous buffer or medium. Additionally, in certain aspects of the present invention, the methods described herein are advantageous because the surfactant compositions can be manufactured on a commercial scale at a significantly lower cost. In certain aspects of the present invention, cost of the manufacturing the process is lowered because the lung surfactant compositions is prepared without the use of a thin film evaporator and/or aseptic environment Accordingly, this invention is, in part, directed to simplified manufacturing processes for producing lung surfactant compositions, lung surfactant compositions with improved viscosity and surface tension characteristics, as well as methods of treating respiratory dysfunction using the lung surfactant compositions. The improved pulmonary surfactant compositions are obtainable by certain methods of this invention as described herein.

In certain embodiments of the present invention, methods for producing a lung surfactant composition comprise the steps of combining a lung surfactant polypeptide and one or more lipids with an organic solvent system to form a substantially homogeneous liquid mixture and lyophilizing the liquid mixture to obtain a lyophilized lung surfactant polypeptide composition. The organic solvent system comprises a sufficient amount of organic solvent to solubilize the lung surfactant polypeptide and one or more lipids and form a substantially homogeneous liquid mixture. In certain aspects of the present invention, the substantially homogeneous liquid mixture is filtered before lyophilization. In certain aspects, the substantially homogeneous liquid mixture is filter sterilized before lyophilization. In some other aspects, the lung surfactant polypeptide composition is sterilized after lyophilization.

The present invention also provides dry lung surfactant composition produced by the methods described herein.

In certain embodiments, the methods of the present invention comprise the steps of obtaining a lyophilized lung surfactant produced by certain methods described herein and reconstituting the lyophilized lung surfactant with a sufficient amount of a pharmaceutically acceptable dispersing agent to yield a liquid lung surfactant composition.

In certain embodiments, the methods of the present invention comprise the steps of treating respiratory dysfunction in a patient comprising administering a lyophilized lung surfactant composition produced by the methods described herein to a patient.

DETAILED DESCRIPTION

A. Introduction

Figure 1:
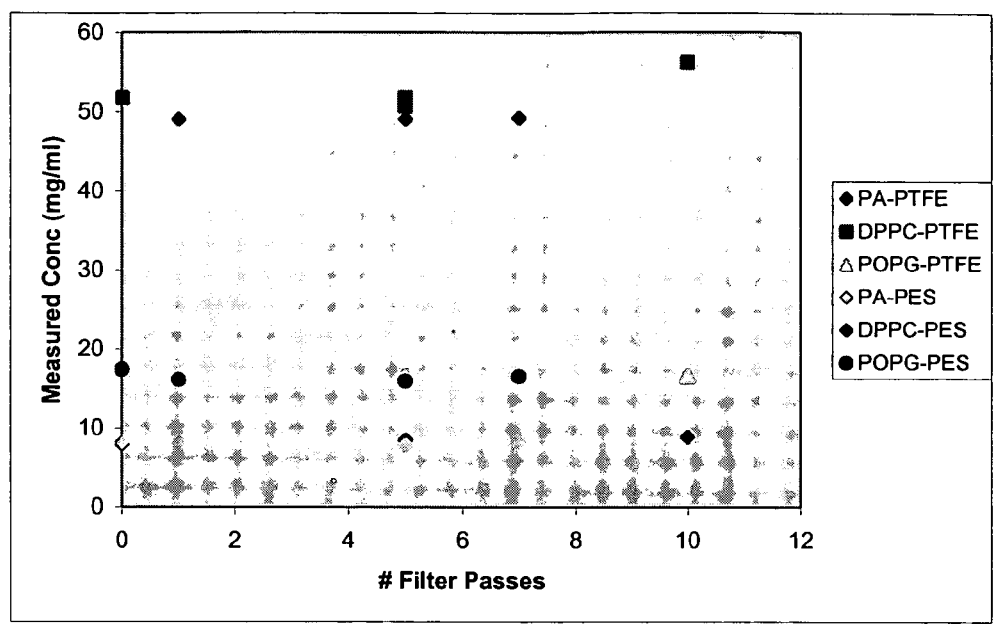
FIG. 1 illustrates the measured concentration of the lipids that are present in exemplary compositions of this invention compared with the number of filter passes during sterile filtration.

The present invention provides, inter alia, liquid lung surfactant compositions. The invention also provides, inter alia, methods of making and methods of using pulmonary surfactants. It has been discovered by the inventors that when a pulmonary surfactant is dispersed in an effective amount of an organic solvent system and subsequently lyophilized, a desirable pulmonary surfactant is formed.

The invention provides a number of methods, reagents, and compounds that can be used for the treatment of respiratory distress dysfunction. It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a surfactant" includes a combination of two or more surfactants, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

All "amino acid" residues identified herein are in the natural L-configuration. In keeping with standard polypeptide nomenclature, *J. Biol. Chem.*, 243: 3557-59, 1968, abbreviations for amino acid residues are as shown in the following table.

| 1-Letter | 3-Letter | Amino Acid |
|---|---|---|
| Y | Tyr | L-tyrosine |
| G | Gly | L-glycine |
| F | Phe | L- |
| M | Met | L-methionine |
| A | Ala | L-alanine |
| S | Ser | L-serine |
| I | He | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gin | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

As described in more detail below, the organic solvent system comprises an organic solvent that is selected from the group consisting of lower oxyhydrocarbons, lower halohydrocarbons, lower haloxyhydrocarons, lower sulfoxyhdyrocarbons, lower cyclohydrocarbons, and combinations thereof.

"Lower oxyhydrocarbons" as referred to herein means compounds possessing hydrocarbyl radicals and oxygen atoms having from 1 to 8 carbon atoms and from 1 to 4 oxygen atoms. Exemplary lower oxyhydrocarbons include, but are not limited to, lower alkanols, lower ketones, lower carboxylic acids, lower carboxylic esters, lower carbonates, and the like.

"Lower" as it refers to chemical compounds described herein refers to those compounds that have from 1 to 8 carbon atoms.

"Lower alkanol" refers to a saturated $C_1$-$C_8$ alkyl group which can be branched or straight-chained with from 1 to 4 hydroxyl groups. Exemplary lower alkanols having 1 hydroxyl group include, but are not limited to, methanol, ethanol, n-propanol, iso-propanol, n-butanol, iso-butanol, 2-butanol, t-butanol, pentanol, iso-pentanol, 2-pentanol, 3-pentanol, t-pentanol, and the like.

Exemplary "lower ketones" include, but are not limited to, acetone, methyl ethyl ketone, methyl propyl ketone, methyl isopropyl ketone, methyl butyl ketone, methyl iso-butyl ketone, methyl 2-butyl ketone, methyl t-butyl ketone, diethyl ketone, ethyl propyl ketone, ethyl isopropyl ketone, ethyl butyl ketone, ethyl iso-butyl ketone, ethyl t-butyl ketone, and the like.

Exemplary "lower carboxylic acids" include, but are not limited to, formic acid, acetic acid, propionic acid, butyric acid isobutyric acid and the like.

Exemplary "lower carboxylic esters" include, but are not limited to, methyl acetate, ethyl acetate, propyl acetate, isopropyl acetate, butyl acetate, isobutyl acetate, 2-butyl acetate, t-butyl acetate, and the like.

Exemplary "lower carbonates" include, but are not limited to, dimethyl carbonate, methyl ethyl carbonate, methyl propyl carbonate, methyl isopropyl carbonate, methyl butyl carbonate, methyl iso-butyl carbonate, methyl 2-butyl carbonate, methyl t-butyl carbonate, diethyl carbonate, ethyl propyl carbonate, ethyl isopropyl carbonate, ethyl butyl carbonate, ethyl iso-butyl carbonate, ethyl t-butyl carbonate, and the like.

"Lower halohydrocarbons" as referred to herein means compounds possessing hydrocarbyl radicals and halo atoms having from 1 to 8 carbon atoms and from 1 to 4 halo atoms. Preferably, the halo atoms are chloro, fluoro and bromo. Most preferably, the halo atoms are chloro atoms. Exemplary lower halohydrocarbons, include, but are not limited to, methyl chloride, methylene chloride, chloroform, carbon tetrachloride, and the like.

"Lower haloxyhydrocarbons" means oxyhydrocarbons as defined herein which are further substituted with from 1 to 4 halo atoms. An exemplary haloxyhydrocarbon includes, but is not limited to, hexafluoroacetone.

"Lower sulfoxyhydrocarbons" means oxyhydrocarbons as defined herein which also contain a sulfur atom. Exemplary lower sulfoxyhydrocarbons include, but are not limited to, dimethyl sulfoxide (DMSO) and dimethyl sulfone.

"Lower cyclohydrocarbons" refers to hydrocarbyl radicals which are cyclized such as, for example 3- to 8- member hydrocarbon rings. An exemplary cyclohydrocarbon includes, but is not limited to, cyclohexane.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as used herein refers to any peptide that possesses a net positive charge at pH 7.4. The biological activity of the peptides can be determined by standard methods known to those of skill in the art and described herein.

Peptides of the invention can be synthesized by methods known in the art. For example, in certain embodiments, commonly used methods such as t-BOC or FMOC protection of alpha-amino groups can be used. Both methods involve stepwise syntheses whereby a single amino acid is added at each step starting from the C terminus of the peptide (See, Coligan et al., *Current Protocols in Immunology*, Wiley Interscience, 1991, Unit 9). Peptides of the invention can be synthesized, for example, by the well known solid phase peptide synthesis methods described in Merrifield, *J. Am. Chem. Soc.* 85: 2149, 1962, and Stewart and Young, 1969, *Solid Phase Peptides Synthesis*, pp. 27-62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

"Recombinant" when used with reference to a protein indicates that the protein has been modified by the introduction of a heterologous nucleic acid or protein or the alteration of a native nucleic acid or protein.

B. Compositions and Methods

Lyophilized lung surfactant polypeptide compositions described herein are typically prepared by combining lung surfactant polypeptide and one or more lipids with an organic solvent system to form a substantially homogeneous liquid mixture, and subsequently lyophilizing the mixture. The mixture can be sterilized before or after lyophilization. In certain embodiments, the substantially homogenous liquid mixture is sterile filtered before lyophilization to obtain a sterile liquid mixture and the sterile mixture is subsequently lyophilized. In certain other embodiments, the lung surfactant composition is terminally sterilized, e.g., sterilized after lyophilization.

Natural lung surfactants are protein/lipid compositions that are produced naturally in the lungs and are critical to the lungs' ability to absorb oxygen. They cover the entire alveolar surface of the lungs and the terminal conducting airways leading to the alveoli. Surfactants facilitate respiration by continually modifying the surface tension of the fluid normally present within the alveoli. In the absence of sufficient surfactant, or should the surfactant degrade, the alveoli tend to collapse and the lungs do not absorb sufficient oxygen. By lowering the surface tension of the terminal conducting airways, surfactant maintains patency, i.e., keeps airways open. Loss of patency leads to loss of patency obstruction of the airway and compromised pulmonary function. Human surfactants primarily contain: phospholipids, the major one being dipalmitoyl phosphatidyl-choline (DPPC), and four surfactant polypepides, A, B, C and D with surfactant protein B (SP-B) being essential for respiratory function.

In preferred aspects, a lung surfactant polypeptide of the present invention is a cationic peptide that can be derived from animal sources or synthetically. Exemplary lung surfactant polypeptides for use herein include naturally and non-naturally occurring lung surfactant polypeptides, such as, for example, animal-derived SP-A, SP-B, SP-C, or SP-D polypeptides; recombinant SP-A, SP-B, SP-C, or SP-D polypeptides; synthetically derived SP-A, SP-B, SP-C, or SP-D polypeptides; SP-A, SP-B, SP-C, and SP-D analogs; SP-A, SP-B, SP-C, and SP-D polypeptide mimics; conservatively modified variants thereof retaining activity; and fragments thereof retaining activity. A lung surfactant mimic is a polypeptide that is engineered to precisely mimic the essential attributes of human surfactant protein. In certain preferred embodiments, the lung surfactant peptide is a cationic peptide that consists of at least about 10, preferably at least 11 amino acid residues, and no more than about 80, more usually fewer than about 35 and preferably fewer than about 25 amino acid residues.

Exemplary amino acid sequences of lung surfactant polypeptides for use herein, methods of isolating them, and producing them by genetic engineering techniques are known in the art. See for example, U.S. Pat. Nos. 5,874,406; 5,840,527; 4,918,161; 5,827,825; 6,660,833, 5,006,343; 5,455,227; 5,223,481; 5,753,621; 5,891,844; 4,861,756; 5,272,252; 5,024,95; 5,238,920; 5,302,481; 6,022,955; 5,874,406; 5,840,527; 5,827,825; 6,660,833; and International Publication Nos., WO8603408 and WO8904326, the disclosures of each of which are hereby incorporated by reference in its entirety. A preferred lung surfactant peptide for use herein is a SP-B or SP-C polypeptide, or polypeptide mimic.

A particularly preferred lung surfactant peptide for use herein is a SP-B polypeptide or polypeptide mimic. SP-B is the protein in natural pulmonary surfactant known to be the most important surfactant protein for surface tension lowering and promoting oxygen exchange. SP-B polypeptide mimics are small hydrophobic polypeptides, generally less than about 80 amino acids in size. Many SP-B polypeptide mimics possess a repeating hydrophobic cationic motif. Like natural SP-B polypeptide, SP-B mimics, preferably, lower surface tension of the terminal conducting airways and promote oxygen exchange.

A preferred SP-B mimetic for use in the present invention is KL4 peptide, which is a cationic peptide containing repeating lysine and leucine residues. KL4 is representative of a family of lung surfactant mimetic peptides which are described, for example, in U.S. Pat. Nos. 5,260,273, 5,164,369, 5,407,914 and 6,613,734, each of which is hereby incorporated by reference in its entirety and for all purposes. Methods of preparing the KL4 peptide can be found in U.S. Pat. No. 5,164,369.

In certain embodiments, lung surfactant polypeptide mimics refer to polypeptides with an amino acid residue sequence that has a composite hydrophobicity of less than zero, preferably less than or equal to −1, more preferably less than or equal to −2. The composite hydrophobicity value for a peptide is determined by assigning each amino acid residue in a peptide its corresponding hydrophilicity value as described in Hopp et al., *Proc. Natl. Acad. Sci.* 78: 3824-3829, 1981, which disclosure is incorporated by reference. For a given peptide, the hydrophobicity values are summed, the sum representing the composite hydrophobicity value.

In certain embodiments, the amino acid sequence of the lung surfactant polypeptide mimic mimics the pattern of hydrophobic and hydrophilic residues of SP18 and perform the function of the hydrophobic region of SP18. SP18 is a known lung surfactant apoprotein, more thoroughly described in Glasser et al., *Proc. Natl. Acad. Sci.* 84: 4007-4001, 1987, which is hereby incorporated by reference in its entirety and for all purposes.

In certain embodiments, SP-B mimics for use herein includes a polypeptide having alternating hydrophobic and hydrophilic amino acid residue regions and is characterized as having at least 10 amino acid residues represented by the formula:

$$(Z_a U_b)_c Z_d$$

Z and U are amino acid residues such that at each occurrence Z and U are independently selected. Z is a hydrophilic amino acid residue, preferably selected from the group consisting of R, D, E and K. U is a hydrophobic amino acid residue, preferably selected from the group consisting of V, I, L, C, Y, and F. The letters, "a," "b," "c" and "d" are numbers which indicate the number of hydrophilic or hydrophobic residues. The letter "a" has an average value of about 1 to about 5, preferably about 1 to about 3. The letter "b" has an average value of about 3 to about 20, preferably about 3 to about 12, most preferably, about 3 to about 10. The letter "c" is 1 to 10, preferably, 2 to 10, most preferably 3 to 6. The letter "d" is 1 to 3, preferably 1 to 2.

By stating that the amino acid residue represented by Z and U is independently selected, it is meant that each occurrence, a residue from the specified group is selected. That is, when "a" is 2, for example, each of the hydrophilic residues represented by Z will be independently selected and thus can include RR, RD, RE, RK, DR, DD, DE, DK, etc. By stating that "a" and "b" have average values, it is meant that although the number of residues within the repeating sequence (ZaUb) can vary somewhat within the peptide sequence, the average values of "a" and "b" would be about 1 to about 5 and about 3 to about 20, respectively.

In certain embodiments, exemplary SP-B polypeptide mimics that can be used in the present invention include, but are not limited to, those shown in the Table of Lung Surfactant Mimetic Peptides.

| Table of Lung Surfactant Mimetic Peptides | | |
|---|---|---|
| Designation[1] | SEQ ID NO | Amino Acid Residue Sequence |
| KL4 | 1 | KLLLLKLLLLKLLLLKLLLLK |
| DL4 | 2 | DLLLLDLLLLDLLLLDLLLLD |
| RL4 | 3 | RLLLLRLLLLRLLLLRLLLLR |
| RL8 | 4 | RLLLLLLLLRLLLLLLLLRLL |
| R2L7 | 5 | RRLLLLLLLRRLLLLLLLRRL |
|  | 6 | RLLLLCLLLRLLLLLCLLLR |
|  | 7 | LLLLLCLLLRLLLLLCLLLRLL |

-continued

Table of Lung Surfactant Mimetic Peptides

| Designation[1] | SEQ ID NO | Amino Acid Residue Sequence |
|---|---|---|
|  | 8 | RLLLLCLLLRLLLLCLLLRLLLLCLLLR DLLLDLLLDLLLDLLLDLLLD |
| RCL1 | 9 | RLLLLCLLLRLLLLCLLLR |
| RCL2 | 10 | RLLLLCLLLRLLLLCLLLRLL |
| RCL3 | 11 | RLLLLCLLLRLLLLCLLLRLLLLCLLLR |
| KL8 | 12 | KLLLLLLLLKLLLLLLLLKLL |
| KL7 | 13 | KKLLLLLLLKKLLLLLLLLKKL |

[1]The designation is an abbreviation for the indicated amino acid residue sequence.

In preferred methods of the present invention, a lung surfactant peptide and one or more lipids are combined with an organic solvent system. The term "lipid" as used herein refers to a naturally occurring, synthetic or semi-synthetic (i.e., modified natural) compound which is generally amphipathic. The lipids typically comprise a hydrophilic component and a hydrophobic component. Exemplary lipids include, but are not limited, phospholipids, fatty acids, fatty alcohols, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion. Preferably, the lipids of the invention are fatty acids, alcohols, esters and ethers thereof and fatty amines.

Examples of phospholipids useful in the compositions delivered by the invention include native and/or synthetic phospholipids. Phospholipids that can be used include, but are not limited to, phosphatidylcholines, phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols useful in these mixtures include, but are not limited to, sterols, palmitic acid, cetyl alcohol, lauric acid, myristic acid, stearic acid, phytanic acid, dipamlitic acid, and the like. Preferably, the fatty acid is palmitic acid and preferably the fatty alcohol is cetyl alcohol.

Examples of fatty acid esters useful in these mixtures include, but are not limited to, methyl palmitate, ethyl palmitate, isopropyl palmitate, cholesteryl palmitate, palmityl palmitate sodium palmitate, potassium palmitate, tripalmitin, and the like.

An example of a semi-synthetic or modified natural lipid is any one of the lipids described above which has been chemically modified. The chemical modification can include a number of modifications; however, a preferred modification is the conjugation of one or more polyethylene glycol (PEG) groups to desired portions of the lipid. Polyethylene glycol (PEG) has been widely used in biomaterials, biotechnology and medicine primarily because PEG is a biocompatible, nontoxic, nonimmunogenic and water-soluble polymer. Zhao and Harris, *ACS Symposium Series* 680: 458-72, 1997. In the area of drug delivery, PEG derivatives have been widely used in covalent attachment (i.e., "PEGylation") to proteins to reduce immunogenicity, proteolysis and kidney clearance and to enhance solubility. Zalipsky, *Adv. Drug Del. Rev.* 16: 157-82, 1995.

Lipids that have been conjugated with PEG are referred to herein as "PEG-lipids."Preferably, when PEG-lipids are used in methods and compositions of this invention, they are present in alcohols and/or aldehydes.

Other excipients can be combined with the lung surfactant polypeptide, one or more lipids, and organic solvent system before lyophilization including, but not limited to, various sugars such as dextrose, fructose, lactose, maltose, mannitol, sucrose, sorbitol, trehalose, and the like, surfactants such as, for example, polysorbate-80, polysorbate-20, sorbitan trioleate, tyloxapol and the like, polymers such as PEG, dextran and the like, salts such as NaCl, $CaCl_2$ and the like, alcohols, such as cetyl alcohol, and buffers.

Preferably, the lung surfactant peptide is combined with phospholipids and free fatty acids or fatty alcohols, e.g., DPPC (dipalmitoyl phosphatidylcholine), POPG (palmitoyloleyl phosphatidylglycerol) and palmitic acid (PA). See, for example, U.S. Pat. No. 5,789,381 the disclosure of which is incorporated herein by reference in its entirety and for all purposes.

In certain preferred embodiments, the lung surfactant composition is lucinactant or another lung surfactant formulation comprising the synthetic surfactant protein KLLLLKLLLLKLLLLKLLLL (KL4; SEQ ID NO:1). Lucinactant, is a combination of DPPC, POPG, palmitic acid (PA) and the KL4 peptide (weight ratio of approximately 7.5:2.5: 1.35:0.267). In certain embodiments, the drug product is formulated at concentrations of, for example, 10, 20, and 30 mg/ml of phospholipid content. In certain other embodiments, the drug product is formulated at greater concentrations, e.g., 60, 90, 120 or more mg/ml phospholipid content, with concomitant increases in KL4 concentration.

Any lung surfactant peptide currently in use, or hereafter developed for use in respiratory distress system and other pulmonary conditions, is suitable for use in the present invention. Current lung surfactant products include, but are not limited to, lucinactant (Surfaxin®, Discovery Laboratories, Inc., Warrington, Pa.), poractant alfa (Curosurf®, Chiesi Farmaceutici SpA, Parma, Italy), and beractant (Survanta®, Abbott Laboratories, Inc., Abbott Park, Ill.).

1. Compositions Prior to Lyophilization

The first step in certain methods of this invention is to obtain a substantially homogenous liquid mixture of the lung surfactant peptide, one or more lipids, in an organic solvent system. By the term "substantially homogeneous" it is meant that the components are uniformly dispersed in each other, for example, as in a solution. In exemplary embodiments, the substantially homogenous mixture will be a solution somewhere in the range of −10° C. to 50° C.

The lung surfactant peptide is preferably dispersed in one or more lipids. The composition containing the lung surfactant peptide and the one or more lipids is sometimes referred to herein as a "colloidal dispersion." To obtain the colloidal dispersion, the lipids are typically admixed with the peptide. Optionally, the lipids and the peptide are admixed in a buffered aqueous medium before combination with the organic solvent system.

In certain preferred embodiments, a mixture of lung surfactant peptide, phospholipids and free fatty acids or fatty alcohols, for example, DPPC (dipalmitoyl phosphatidylcholine) and POPG (palmitoyl-oleyl phosphatidylglycerol) and palmitic acid (PA) is combined with the organic solvent system to form the substantially homogenous liquid mixture. The individual components can be present in the mixture in any concentration. The total concentration of phospholipid in the dispersion can range, for example, from about 1 to over about 80 mg-total phospholipid content/ml. Suitable buffers include, but are not limited to, tris acetate, tris hydrochloride, sodium phosphate, potassium phosphate, and the like. The buffers are typically commercially available.

A particularly preferred colloidal dispersion for use in the methods of the present invention comprises a dispersion of DPPC, POPG, PA and KL4 (weight ratio of approximately 7.5:2.5:1.35:0.267) in a physiologically acceptable aqueous buffer.

Exemplary methods of the present invention include a step of combining a lung surfactant composition and one or more lipids with an organic solvent system. The organic solvent system comprises an organic solvent. The organic solvent system contains a sufficient amount of organic solvent to solubilize the lung surfactant peptide and lipids to form a substantially homogenous liquid mixture. In certain exemplary embodiment, the organic solvent is from about 20% by volume to about 100% by volume of the organic solvent system. In some other embodiments, the organic solvent is from about 20% by volume to about 70% by volume of the organic solvent system. In some other embodiments, the organic solvent is from about 40% by volume to about 60% by volume of the organic solvent system. In certain preferred embodiments, the organic solvent is about 40%, 50%, 60% or 70% by volume of the organic solvent system. In an exemplary embodiment, the organic solvent system further comprises an aqueous medium, such as water. When the organic system comprises two or more components, it is generally in the form of an emulsion or a miscible solution. What is meant by "emulsion" is a colloid in which both phases are liquids and are typically immiscible in one another. A "miscible solution" means two liquids that are capable of mixing. In certain embodiments, the organic solvent system further comprises additional excipients, including, but not limited to, various sugars such as dextrose, fructose, lactose, maltose, mannitol, sucrose, sorbitol, trehalose, and the like, surfactants such as, for example, polysorbate-80, polysorbate-20, sorbitan trioleate, tyloxapol and the like, polymers such as PEG, dextran and the like, salts such as NaCl, $CaCl_2$ and the like, alcohols, such as cetyl alcohol, and buffers. In certain preferred embodiments, the organic solvent system is substantially free of salt. In certain preferred embodiments, the organic solvent system is substantially free of NaCl.

In certain embodiments, the organic solvent system can be prepared by combining all of the system components. For example, in certain embodiments wherein the organic solvent consists of organic solvent and an aqueous medium at room temperature, the aqueous medium and organic solvent can be combined to make up the organic solvent system. Preferably, the organic solvent system is an emulsion or a miscible solution.

The organic solvent selected is preferably compatible with sterile filtration and lyophilization. Solvents utilized in this invention preferably have desirable freezing and partial pressure measurements so as to be able to be collected in a freeze-dryer condenser. In certain exemplary embodiments, the solvent selected has a freezing temperature of about −60° C. to about 40° C. Preferably, solvents of this invention are selected from the group consisting of lower oxy hydro carbons, lower halohydrocarbons, lower haloxyhydrocarbons, lower sulfoxyhydrocarbons, lower cyclohydrocarbons and combinations thereof.

Suitable solvents for use in this invention, include, but are not limited to, isopropyl alcohol, methanol, ethanol, acetone, acetonitrile, cyclohexane, chlorobutanol, dimethylsulfoxide, t-butanol, hexanol, benzyl alcohol, acetic acid, pentanol (1-pentanol), n-butanol, n-propanol, methyl acetate, dimethyl carbonate, methyl ethyl ketone, methyl isobutyl ketone, carbon tetrachloride, hexafluoroacetone, chlorobutanol, dimethyl sulfone, cyclohexane, and combinations thereof. Preferable solvents include lower alkanols, such as t-butanol, ethanol, isopropyl alcohol, and the like.

A particularly preferred solvent of the invention is t-butanol. t-Butanol is a widely employed solvent that is utilized for a variety for pharmaceutical uses. It has often been used as an alternative solvent in the preparation of liposome and other colloidal dispersions and exhibits physico-chemical properties that lend itself for use in lyophilization processes. T-Butanol has a melting point of 23-26 ° C. and a boiling point of 83 ° C. Thus, in some respects it has similar properties to that of water and because it is volatile, it is readily removed during typical lyophilization cycles.

In certain embodiments, the organic solvent and the colloidal dispersion comprising the lung surfactant peptide and one or more lipids are combined at room temperature and then mixed by vortexing to form the substantially homogenous liquid mixture. Typically, the mixing takes from about 1 to about 5 minutes. Optionally, this may be followed by sonication, use of a static mixer, blade mixer, homogenizer and the like. Alternative methods of mixing the organic solvent and colloidal dispersion to form the substantially homogenous liquid mixture can be used in the present methods.

In certain exemplary embodiments of the present invention, the relative amounts of lung surfactant peptide, phospholipids and free fatty acids or fatty alcohols is about 1 part by weight of a lung surfactant peptide; about 20 to about 150 parts by weight of a phospholipid per part weight of the lung surfactant peptide; about 0 to about 25 parts by weight of a free fatty acid or fatty alcohol per part weight of the lung surfactant peptide. In certain embodiments the relative amount of organic solvent system is at least about 500 parts by weight per part weight of the lung surfactant peptide. In certain embodiments, the organic solvent system is present in about 500 to about 50,000 parts by weight per part weight of the lung surfactant peptide. In certain exemplary embodiments, the relative amounts of lung surfactant peptide, phospholipids and free fatty acids or fatty alcohols is about 1 part by weight of a lung surfactant peptide, such as, for example, KL4; about 20 about 100 parts by weight of DPPC; 0 to about 50 parts by weight of POPG; and about 0 to about 25 parts by weight of palmitic acid.

2. Filtration

In certain embodiments of the present invention, after the lung surfactant peptide, one or more lipids, and organic solvent system are combined to form the liquid mixture, the mixture is sterilized. In some embodiments, the substantially homogenous liquid mixture is filter sterilized before lyophilization. This step is performed to remove any contaminants in the liquid mixture and provide a relatively sterile mixture. What is meant by "sterilized" or "relatively sterile" is that any contaminants are present in such a low amount that the product's integrity and/or uniformity is not compromised.

It is contemplated that this optional step of filter sterilization before lyophilization reduces the steps involved in aseptic processing, that are presently required by the current commercial manufacturing method. It is further contemplated that this step also removes the need of the costly thin film evaporator.

Suitable filters include sterile filters that are compatible with organic solvents. The skilled practitioner will understand that the particular filter used is not critical to the present invention. A suitable filter includes, for example, a cellulose filter. A particularly preferred filter is one made of poly(tetrafluoroethylene) (PTFE) because it is generally compatible with alcohols and related organic or organic-aqueous media, including t-butanol. Another preferred filter is composed of poly(ether-sulfone). Other filters compatible with organic-aqueous mixtures include, but are not limited to, polyvinylidene fluoride, polypropylene and nylon.

In certain exemplary embodiments, the porosity of the filter will be from about 0.2 to about 0.45 microns. The size of the filter will determine the volume of the liquid mixture that can be passed through the filter.

After filtration, the compositions can be placed in suitable lyophilization vials. The vials can be single dose formulations following reconstitution.

The vials are generally aseptic and can range from about 5 to about 100 milliliter vials with a fill volume of about 5 to about 75 ml per vial.

In certain embodiments of the present invention, the lung surfactant peptide composition is terminally sterilized, e.g., sterilized after lyophilization. In certain embodiments, terminal sterilization is by autoclaving, gamma irradiation, or e-beam sterilization.

3. Lyophilization

Exemplary methods of the present invention include a step of lyophilizing the lung surfactant mixture. Lyophilizing can occur before or after sterilization.

Lyophilization is the technical name for a process often referred to as "freeze-drying". In this process, an aqueous mixture or suspension is frozen into a solid, then it is generally subjected to a vacuum for a substantial period of time. The vacuum causes the water molecules to "sublimate", i.e., to become gaseous and leave the solid, without going through a liquid state.

In preferred embodiments, during the lyophilization process, the organic solvent system, e.g., water and lower alkanol, is substantially removed by sublimation. In preferred embodiments, less than 5% residual solvent remains after lyophilization, preferably less than 3%, more preferably less than 2% and even more preferably less than 1% or less than 0.1%.

Any method of lyophilization can be used in the present invention. Methods of lyophilization are known in the art and are thus not described herein in detail.

An exemplary lyophilization process comprises the following steps: (1) the sample is placed in the lyophilization chamber and the shelf temperature is lowered to about −40° C. to about −20° C. at about atmospheric pressure; (2) the shelf temperature is held at the temperature range until the sample temperature reaches −40° C. to about −20° C.; (3) the pressure is then reduced to about 50 mTorr to about 600 mTorr and the shelf temperature is increased to from about −20° C. to about 20° C. and held until sublimation of organic solvent system is substantially complete; and (4) the samples are allowed to reach from about −20° C. to about 20° C. at which point the vials are aseptically sealed.

The lyophilization step will produce a lung surfactant peptide composition, e.g., KL4 lung surfactant peptide composition, that can be stored at room temperature for extended periods. It is noted that there will be residual water, and potentially residual organic solvent present in amounts designed to minimize adverse effects on shelf-stability. For example, in certain preferred embodiments, the final moisture content of the dried lung surfactant peptide composition will be less than about 5% by weight, preferably less than 2.5% by weight, more preferably less than about 3% by weight and most preferably, less than about 1.5% by weight.

The lyophilized lung surfactant peptide composition will be a dry composition. In certain embodiments, the lyophilized lung surfactant peptide composition will be in the form of a cake or free flowing powder. In preferred embodiments, the lyophilized lung surfactant peptide composition will be in the form of a cake.

4. Reconstitution

In certain exemplary embodiments, the lyophilized pulmonary surfactant composition readily reconstitutes once contacted with a sufficient amount of a pharmaceutically acceptable dispersing agent. For example, in certain embodiments, the lyophilized lung surfactant composition is mixed, e.g., shaken for about 1 to about 10 minutes, with a dispersing agent to provide a liquid lung surfactant composition. The dispersing agent is preferably sterile water. The liquid lung surfactant composition can be further diluted with isotonic saline or other excipients to produce a desirable concentration prior to administration.

In exemplary embodiments of the present invention, the liquid lung surfactant compositions that are produced exhibit desirable characteristics, such as desirable viscosity and surface tension characteristics.

Lung surfactant compositions ideally have low surface tension values so as to enable them to flow easily or spread across the surface of the lungs.

The term "surface tension" refers to the attractive force exerted by the molecules below the surface upon those at the surface/air interface, resulting from the high molecular concentration of a liquid compared to the low molecular concentration of the gas. Liquids with low values of surface tension, such as nonpolar liquids, flow more readily than water. Typically, values of surface tensions are expressed in newtons/meters or dynes/centimeters.

"Dynamic surface tension" as referred to herein is the surface/air interface and the dynamic interfacial tension to the surface/surface interface. There are a number of alternative methods for measuring dynamic surface tension, for example, captive bubble surface tensionometry or pulsating bubble surface tensionometry. One preferred method of measuring dynamic surface tension is the pulsating bubble surface tensionometry provided below.

In one exemplary embodiment, the dynamic surface tension of a lung surfactant composition is measured at 3 mg or 10 mg-total phospholipid content (TPL)/ml using a Pulsating Bubble Surfactometer (PBS, Electronetics Corp, Seminole, Fla.). The sample is diluted in 20 mM Tris-Ac buffer at pH 7.6 containing 130 mM NaCl. Upon dilution, the sample is vortexed for 10 seconds and heated in a 37° C. water bath for 10 minutes. After removal from the water bath, the sample is vortexed for 10 seconds. Approximately 50 μL of sample is analyzed on the PBS at 37° C. A bubble is formed by the user and allowed to equilibrate for 1 minute. The bubble is then pulsated at an oscillation frequency of 20 cycles/min for 6 minutes, during which time the bubble cycled from a minimum radius of 0.4 mm to a maximum radius of 0.55 mm. The pressure transducer in the PBS instrument measures a pressure, which is used to calculate the surface tension using the Laplace equation. The surface tension after 100 cycles is determined and reported as the minimum dynamic surface tension of the sample Preferred lung surfactant compositions of the present invention exhibit low surface tensions. In certain embodiments, the present invention provides lung surfactant compositions that exhibit a low dynamic surface tension of less than less than about 10 mN/m at a concentration of 10 mg-TPL/ml in Tris-Ac buffer at pH 7.6 containing 130 mM NaCl at an oscillation frequency of 20 cycles/minute at 37° C. with the bubble radius varying between 0.4 and 0.55 mm using an Electronetics Corporation Pulsating Bubble Surfactometer (PBS) and as measured after 5 minutes of cycling. In certain embodiments, the lung surfactant compositions will exhibit a dynamic surface tension of less than less than about 5 mN/m at a concentration of 10 mg-TPL/ml or less than about 5 mN/m at a concentration of 3 mg-TPL/ml.

Additionally, lung surfactants also have a low viscosity so as to allow the composition to distribute effectively in the lung. In addition, a less viscous product is easier to handle and administer.

The term "viscosity" refers to the internal resistance to flow exhibited by a fluid at a specified temperature; the ratio of shearing stress to rate of shear. A liquid has a viscosity of one poise if a force of 1 dyne/square centimeter causes two parallel liquid surfaces one square centimeter in area and one square centimeter apart to move past one another at a velocity of 1 cm/second. One poise equals one hundred centipoise.

When referring to apparent viscosity, it is understood that the value of viscosity is dependent on the conditions under which the measurement was taken, such as temperature, the rate of shear and the shear stress employed. The apparent viscosity is defined as the ratio of the shear stress to the rate of shear applied. There are a number of alternative methods for measuring apparent viscosity. For example, viscosity can be tested by a suitable cone and plate, parallel plate or other type of viscometer or rheometer. One preferred method of measuring apparent viscosity is using a rheometer, as provided below.

In one exemplary embodiment, the apparent viscosity of a surfactant formulation is measured at a temperature of 25° C. using a rheometer (e.g., TA AR1000 Rhemoeter, TA Instruments, New Castle, Del. fitted with a 40 mm/1° acrylic cone). Approximately 350 μL of undiluted surfactant is placed on the rheometer and allowed to thermally equilibrate at 25° C. A step flow procedure is utilized to analyze the samples with a linear increase in the shear rate with time (0 to 200 sec$^{-1}$) followed by linear decrease in shear rate (200 to 0 sec$^{-1}$). During each ramp up and ramp down process, 15 points are collected resulting in approximately 6 minutes of total run time. The viscosities measured at a shear rate of 157 sec$^{-1}$ during the ramp up and ramp down ar averaged and reported as the apparent viscosity for each sample.

Exemplary liquid lung surfactant composition prepared by the methods described herein exhibit an apparent viscosity of less than about 50 cP at a concentration of 30 mg-TPL/ml when measured at a temperature of 25° C. and a shear rate of 157 sec$^{-1}$ using a rheometer fitted with a 40 mm/1° acrylic cone, and a step flow procedure with a linear increase in shear rate with a time of 0 to 200 sec$^{-1}$ over approximately 3 minutes followed by a linear decrease in shear rate with a time of 200 sec$^{-1}$ to 0 sec$^{-1}$ over approximately 3 minutes. In certain embodiments, exemplary liquid lung surfactant composition prepared by the methods described herein exhibit an apparent viscosity of less than about 30 cP at a concentration of 30 mg-TPL/ml or even less than about 15 cP at a concentration of 30 mg-TPL/ml.

5. Administration

The lung surfactant composition described herein can be used in the treatment of various respiratory disorders or in replacement therapy and are particular useful in the rescue and prophylactic treatment of infants with RDS (respiratory distress syndrome) and in adults with ARDS (acute respiratory distress syndrome). Both the dry and the liquid surfactants prepared by methods of this invention can be administered to patients in need of respiratory therapy. Specifically, the dry lung surfactant compositions can be further processed and administered, for example, as a dry powder of an aerosol and the liquid lung surfactant can be administered, for example, as a liquid bolus or as a wet aerosol.

When used as an aerosol preparation, the surfactant composition can be supplied in finely divided form, optionally in combination with a suitable propellant. Useful propellants are typically gases at ambient conditions and are condensed under pressure including, for example, lower alkanes and fluorinated alkanes, such as freon. In certain embodiments wherein the surfactant composition is delivered as an aerosol, the aerosol can be packaged in a suitable container under pressure. In certain alternative embodiments, the lyophilized powders can be further processed by milling or other means for incorporation as unit or multi-dose packets within dry powder inhaler systems. Suitable dosage of the surfactant, whether aerosolized or delivered as a liquid bolus will be dependent on the patient's age and severity of the disorder and will be readily ascertainable by the attending clinician. The actual dosage of lung surfactant will of course vary according to factors such as the extent of exposure and particular status of the subject (e.g., the subject's age, size, fitness, extent of symptoms, susceptibility factors, etc). By "effective dose" herein is meant a dose that produces effects for which it is administered.

Pulmonary surfactant finds particular utility in critical care settings, specifically in supplying lung surfactant to prematurely born infants but also with patients with acute respiratory distress syndrome, acute lung injury, meconium aspiration syndrome and the like.

When the surfactant is supplied to prematurely born infants, an aliquot of the surfactant composition is delivered, preferably by intratracheal instillation, to provide an effective dose of surfactant in the lungs of the treated patient. Preferably, a single surfactant dose ranges from, for example, about 20 to about 300 mg-TPL/kg, more preferably from about 60 to about 175 mg-TPL/kg. It being understood, of course, that the exact dose of surfactant will depend upon factors such as the age and condition of the patient, the severity of the condition being treated, and other factors well within the skill of the attending clinician. In certain embodiments wherein the surfactant composition is delivered as an aerosol, such as disclosed in co-pending U.S. application Ser. No. 11/130,783, filed May 17, 2005, incorporated herein by reference in its entirety, the effective dose of lung surfactant will be, for example, from about 2 mg-TPL/kg surfactant to about 175 mg-TPL/kg surfactant. Other methods of delivery include lavage, lung wash, and the like. When so employed dose ranges are well within the skill of one in the art.

In addition, the methods and systems are also useful in treating other clinical disorders as seen in infants and other pediatric patient populations such as, by way of example cystic fibrosis, intervention for infectious processes, bronchiolitis, and the like.

It is contemplated that patients that could benefit from the lung surfactant compositions described herein ranges from premature infants born at about 24 weeks gestation to adults.

Patients inflicted with other respiratory disorders can benefit from the methods and systems of the invention. These respiratory disorders include, for example, but are not limited to, the disorders of neonatal pulmonary hypertension, neonatal bronchopulmonary dysplasia, chronic obstructive pulmonary disease, acute and chronic bronchitis, emphysema, bronchiolitis, bronchiectasis, radiation pneumonitis, hypersensitivity pneumonitis, acute inflammatory asthma, acute smoke inhalation, thermal lung injury, asthma, e.g., allergic asthma and iatrogenic asthma, silicosis, airway obstruction, cystic fibrosis, alveolar proteinosis, alpha-1-protease deficiency, pulmonary inflammatory disorders, pneumonia, acute respiratory distress syndrome, acute lung injury, idiopathic respiratory distress syndrome, idiopathic pulmonary fibrosis, sinusitis, rhinitis, tracheitis, otitis, and the like. Accordingly, the present invention provides methods, systems, and devices for treating these diseases in a patient.

In certain embodiments, methods of the present invention for producing lung surfactant compositions are an improvement to the scalability of surfactant production, reproducibility of uniform product and the ease of manufacturing over the current commercial product.

The following examples are set forth to illustrate the claimed invention and are not to be construed as limitations thereof.

EXEMPLARY EMBODIMENTS

Unless otherwise stated, all temperatures are in degrees Celsius. Also, in these examples and elsewhere, the following abbreviations have the following meanings:

| | |
|---|---|
| ml = | milliliter |
| v/v = | volume/volume |
| mg = | milligram |
| HPLC = | high performance liquid chromatography |
| TPL = | total phospholipids |
| μl or um = | milliliter |
| mN/m = | millinewton/meter |
| m = | meter |
| cP = | centipoise |
| PSA = | particle size analysis |
| PBS = | pulsating bubble surface tensionmetry |
| μm or um = | millimeter or micron |
| RT = | room temperature |
| min = | minute |
| TBA = | t-butanol |

EXAMPLE 1

Organic Solvent System and Melting Point

To determine a temperature range for solvent mixtures in which they remained liquid, solutions of 100, 95, 90, 80, and 50% v/v (volume per volume) t-butanol in aqueous buffer were prepared and equilibrated at room-temperature (e.g., 25° C. ), 2 to 8° C., and −20° C. Observations were made as to whether the solutions were solid or liquid. Neat t-butanol typically freezes at 25.4° C. Addition of water to t-butanol depressed the melting point as illustrated in Table 1. That is, 95, 90, 80, and 50% v/v t-butanol solutions all remained liquid both at room temperature as well as when stored at 2-8° C. These data indicate that storage and/or utilization the t-butanol/water mixtures in a refrigerated environment or warmer would not be inhibited by a phase transition (i.e., freezing).

TABLE 1

| t-butanol | Water | RT (~26° C.) | Refrigerator (2-8° C.) | Freezer (−20° C.) |
|---|---|---|---|---|
| 100% | 0% | liquid | solid | solid |
| 95% | 5% | liquid | liquid | solid |
| 90% | 10% | liquid | liquid | solid |
| 80% | 20% | liquid | liquid | solid |
| 50% | 50% | liquid | liquid | solid |

EXAMPLE 2

Solubility Measurements i. Individual Component Solubilites

Aliquots of each lipid and peptide were accurately weighed into 1.5 ml Eppendorf tubes. Target weights were approximately 25 mg for DPPC, POPG and palmitic acid (PA), 50 mg for cetyl alcohol (CA) and 10 mg for KL4. To each tube 0.2 ml of solvent was added. Each tube was vortexed and then bath sonicated for several minutes to facilitate dissolution. Samples were then placed in a 37° C. bath for approximately 30 minutes and then removed and placed on the counter for up to 30 minutes. Hence the temperatures upon sampling were between 25 and 37° C. Three independent Eppendorf tubes were prepared and tested for each solute-solvent combination. Visual observations were made of each tube as to whether they appeared a) clear (i.e., apparently fully soluble), b) to contain non-dissolved material, or c) indeterminate. Small aliquots of each tube were then taken, diluted in the HPLC running buffer, and analyzed by HPLC. HPLC was performed using a CIS column by established methods.

The results of the solubility measurements for the individual lipids and KL4 into t-butanol/water solutions at about 37° C. are shown in Table 2. Many of the test conditions resulted in the complete solubilization of the lipid and/or peptide at about 37° C. This was evidenced both by visual observation of each sample/tube as well as by comparing the HPLC-determined concentrations with sample weights divided by the solvent volumes (data not shown). A minimum value of the solvent solubility can be found in Table 2. POPG was largely insoluble in 100% and 99% t-butanol with the concentration below the detection limit of the assay, which was approximately 5 mg/ml. As such, an upper limit of the solubility can be found in Table 2.

TABLE 2

| Target* | Solubility (mg/ml) | | | | | | |
|---|---|---|---|---|---|---|---|
| (mg/ml) | 100% | 99% | 97.5% | 95% | 90% | 80% | 50% |
| DPPC 22.5 | >150 | nt | nt | >150 | >145 | >133 | >49 |
| POPG 7.5 | <5 | <5 | 20 | 34 | >160 | >119 | >47 |
| PA 4.05 | >130 | nt | nt | >150 | >151 | >140 | 20 |
| CA 4.05 | >270 | nt | nt | >251 | >229 | >224 | 14 |
| KL4 0.937 | 34 | nt | nt | 29 | >92 | >36 | >67 | nt = not tested
*assuming 30 mg TPL/ml for filling/lyophilizaton

Table 2 shows that the lipids and KL4 are generally very soluble in t-butanol-water solutions relative to the target concentrations that would be viable for a manufacturing process (target concentration assumed to be 30 mg/ml TPL for filling/lyophilization). The only condition in which the target was not met was for POPG at 100% and 99% t-butanol.

ii. Lipid/KL4 Combined Solubilities

In addition to the solubility measurements for individual components, lipids and KL4 were also combined and tested for dissolution in t-butanol-water solutions at 30 mg/ml total phospholipid content (TPL) with nominal KL4 surfactant composition.

That is, DPPC, POPG, PA and KL4 were weighed and combined into a 20 ml scintillation vial at weight ratios of 3:1:0.54:0.107. The appropriate volume of solvent (i.e., 12 ml achieved 30 mg/ml TPL) was added to obtain 95, 90, 80, 70, 60, 50, 40 and 30% v/v t-butanol. Vials were bath sonicated at about 50° C. and gently stirred for about 1 to 3 minutes until the solutions became clear. Visual observations were made as to solubility (all were completely transparent) as well as HPLC measurements on the final solution.

All solutions fully solubilized the lipids and KL4 at 30 mg/ml (visual observation) after 1-3 minutes of bath sonication at 50° C. HPLC analysis on the solutions for lipids and KL4 content confirmed the visual observation of complete solubilization.

EXAMPLE 3

Filtration Recoveries

Poly(tretrafluoroethylene) (PTFE) is a material that is compatible with alcohols in general and t-butanol in particular. Moreover, Sartorius manufactures a line of sterile filters for aseptic manufacturing processes utilizing PTFE Sartofluor®. Sartofluor® syringe filters were obtained to identify the levels of lipid and peptide retention on the filter system. Syringe filters composed of poly(ether-sulfone) (PES) were also evaluated.

i. Filtration of 90%v/v t-butanol Solution

Lipids and peptide were weighed and combined dry in a 20 ml scintillation vial (450 mg DPPC, 150 mg POPG, 81 mg PA, and 15.9 mg KL4 (purity adjusted)). To this vial, 10 ml of 90% v/v t-butanol was added. Note that the 90% v/v t-butanol solvent composition was selected based upon the solubility. The solution was warmed to 37° C. and bath sonicated for several minutes to dissolve the components. The 90% v/v t-butanol lipid solutions were serially passed through the same PTFE and PES filter 10 consecutive times (about 5 ml per filter). Aliquots (200 ul) were taken for HPLC testing after 0,1, 5, 7 and 10 passes through the filter. Control groups of solvent alone were passed through the filter and tested on HPLC to ensure that no leachables were detectable.

No significant pressure differences were observed in passing the solvents alone or solvents plus lipids/KL4 through the either the PTFE or PES filters. That is, all solutions appeared to readily pass through the PTFE and PES filters.

Figure 2:
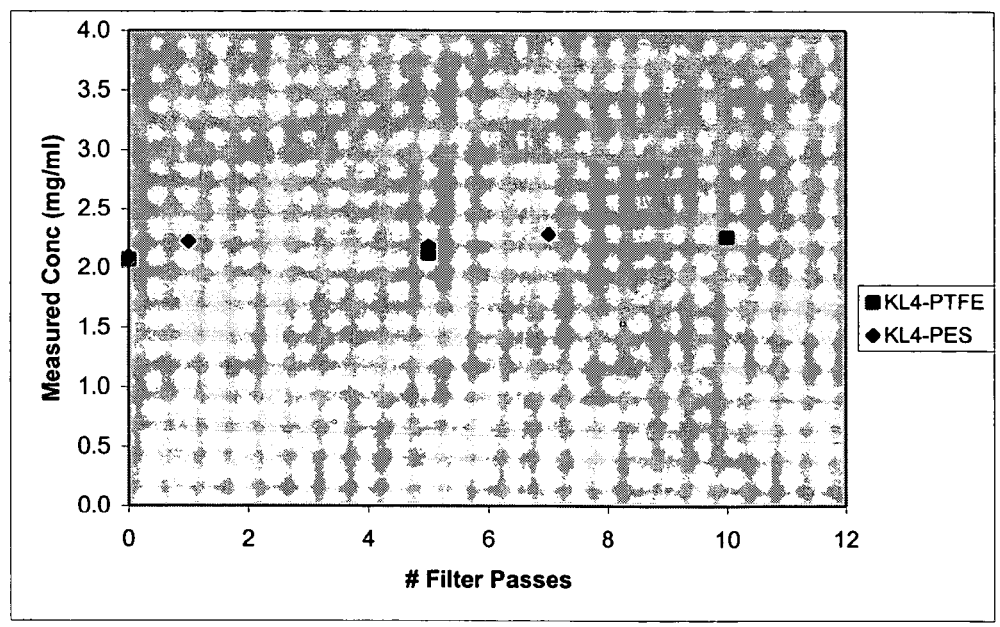
FIG. 2 illustrates the measured concentration of the KL4 polypeptide that is present in exemplary compositions of this invention compared with the number of filter passes during the sterile filtration. This is a measurement of the KL4 after extraction from the lipids.

The HPLC results from the sterile filtration study with 90% v/v t-butanol are shown in FIG. 1 and 2. No significant change in lipid or KL4 concentrations were observed for the 0-10 passes through the PTFE and PES filters.

ii. Filtration of 40-70%v/v t-butanol Solutions

A filtration study was performed by passing 30 mg/ml TPL solutions of 70, 60, 50 and 40% v/v t-butanol through the Sartorius PTFE syringe filters described above. The TPL solutions contained 270 mg DPPC, 90 mg POPG, 48.6 mg PA, and 9.5 mg KL4 (purity adjusted) dissolved in 12 ml of solvent. Samples of each lipid/KL4 solution were taken and analyzed by HPLC before and after one pass through the filter.

Results from the filtration study of 70, 60, 50, and 40% v/v t-butanol containing lipid and KL4 at 30 mg/ml TPL are shown in Table 3. That is, the measured concentration of each component after filtration relative the measured concentration prior to filtration is recorded as and referred to as recovery. Table 3 shows that no significant loss of lipids occurred during the filtration with 70, 60, 50, and 40% t-butanol, consistent with the observations above for 90% v/v t-butanol. Recoveries were between 95 and 102% of starting concentrations and were, on average, 99, 99, and 98% for PA, DPPC, and POPG, respectively.

TABLE 3

| | Post Filtration Recovery | | |
|---|---|---|---|
| | PA | DPPC | POPG |
| 40% | 97% | 100% | 98% |
| 50% | 100% | 99% | 99% |
| 60% | 95% | 96% | 95% |
| 70% | 102% | 100% | 101% |
| Ave | 99% | 99% | 98% |
| Stdev | 3% | 2% | 3% |

EXAMPLE 4

Lyophilization

The initial lyophilization cycle that was used consisted of:
1. Shelf temperature lowered to −30° C. at atmospheric pressure.
2. Shelf temperature held at −30° C. until sample temperature reaches −30° C.
3. Pressure reduced to 500 mTorr and shelf temperature increased to 0° C.
4. Cycle is complete once samples have reached 0° C.

Part A

Lyophilization vials (20 ml) were filled with 2 ml of 30 mg/ml KL4 lung surfactant containing DPPC (45 mg), POPG (15 mg), PA (8.1 mg) and KL4 (1.6 mg), dissolved in 95, 90, 80 and 50% v/v t-butanol, three vials per condition. Samples were lyophilized as per above cycle. Lyophilized cakes were assayed by time of hydration with Tris-NaCl at room temperature, pulsating bubble surface tensionometry (PBS), viscosity, and particle size analysis (PSA).

The lipids-KL4 solids all solubilized in the selected solvents at 30 mg/ml TPL. All solvent compositions produced, cylindrical white cakes that were stable to mild shock (i.e., normal handling).

The time of hydration using a wrist action shaker varied with the initial solvent composition. The cake formed from 50% v/v t-butanol hydrated in less than the minimum 5-minute time setting on the wrist action timer, while the cake formed from 95% v/v t-butanol did not fully hydrate the lipids with in 35 minutes. All reconstituted formulations exhibited good surface activity readings of about 0 mN/m measured at 3 mg/ml TPL. The viscosities of the hydrated formulations varied considerably. The lowest viscosity was measured from the "50% t-butanol"formulation, 17 cP, while the highest viscosity reading from the "95% t-butanol"formulation was nearly one-log greater, 165 cP.

Part B

Each 20 ml lyophilization vial was filled with 2 ml of 30 mg/ml lung surfactant consisting of DPPC, POPG, PA and KL4 dissolved in 95, 90, 80, 70, 60, 50, 40, and 30% v/v t-butanol. The amounts of each component were the same as in part A. Five vials were prepared for each condition.

All solvent compositions fully solubilized the lipids/KL4. The post-lyophilization cakes from all solvents were cylindrical, white, and stable to normal handling. The moisture contents of the cakes are all fairly low, 1.0 to 2.3% as measured by Karl-Fischer titration, and did not show a clear trend. Apparent viscosity decreased as the t-butanol content decreased but surface activity was excellent, as measured by PBS, for all compositions tested.

EXAMPLE 5 i. Solvent Preparation

Each of the solvent mixtures (40, 50, 60, 70 and 80% TBA) were prepared by weight in DI water.

ii. Combined Solid Lipid Components Preparation

For ease of preparation and to reduce the amount of weighing that would be required for measuring the solubility of all 4 components in the solvent mixtures, dry lipid compositions were prepared by lyophilizing an aqueous 30 mg/ml solution of the lipids, prepared by the post-TFE process. Two such formulations were prepared. One of the formulations was hydrated with DI water and the second formulation was hydrated with Tris-A, pH 7.6 buffer. Hydration was carried out on the same day as filling the vials, so as to ensure lower viscosity and therefore ease of handling. 10 mL vials were then filled with target formulation fills (by weight) to achieve 30, 45, 60, 90 and 120 mg/ml concentrations both for formulations with and without NaCl. All vials were semi-stoppered and thermocouples were placed in one representative vial for each concentration.

Sample vials were freeze-dried and primary drying was extended up to 4000 minutes to ensure complete drying of the samples, as indicated by both thermocouple and TCVG readings. In addition to visual observation of the dried cakes post lyophilization, residual moisture was measured by a Karl Fischer method for each of the thermocouple vials to confirm that low moisture was achieved.

Co-solvent mixtures were allowed to thermally equilibrate to room temperature in the lab prior to accurately adding by weight the prescribed amount to each vial. Following solvent addition, the vial contents were mixed gently. Solubility was recorded initially by visual observation (i.e. denoting one of the following: clear solution, cloudy, phase-separated, large aggregates, small aggregates, gel). Samples which were not fully solubilised by gentle mixing were bath sonicated at 30° C. until clear or for a maximum duration of 5 minutes. Samples subjected to sonication at 30° C. were re-equilibrated to room temperature for a minimum period of 2 hours. Component solubilities (quantification of DPPC, POPG, PA and KL4) were measured by HPLC of clear supernatant, obtained by centrifugation at 22° C. of a 1 ml sample from each vial.

Formulations were prepared with NaCl and without NaCl at each of the solvent compositions to be tested. For this study, target weights for 9.1 ml fills were determined and each formulation composition was weighed out into 20 ml vials. All vials were semi-stoppered and configured on the shelf of the freeze-dryer.

Sample vials were freeze-dried using a simple lyo cycle, more specifically by freezing to −40° C., pulling a vacuum in the chamber to 200 mT and setting the shelf temperature to 5° C. Primary drying was extended up to 4000 minutes to ensure complete drying of the samples, as indicated both by product thermocouples (which were placed in the central and two extreme corner vials as indicated in FIG. 2) and TCVG readings.

iii. Product Properties

A. Cake Appearance and Reconstitution Time

Uniform cakes were observed for all formulations, exhibiting cylindrical properties with no evidence of collapse or melt-back. Cakes were off-white in color and were also robust with no tendency to collapse into a loose powder. Reconstitution times for all cakes are summarized in Table 4. Of particular note here is that the observations for this study were based on the reconstitution of one vial in each case.

TABLE 4

Summary of reconstitution times for a range of lyophilized TBA cosolvent formulations with and without salt

| TBA (%, w/w) | Recon Time | Observations |
|---|---|---|
| w/o NaCl | | |
| 40% | 45 sec | homogenous |
| 50% | 45 sec | homogenous |
| 60% | 60 sec | homogenous |
| 70% | 60 sec | lumps |
| 80% | 60 sec | homogenous |
| With NaCl | | |
| 40% | 30 sec | homogenous |
| 50% | 15 sec | homogenous |
| 60% | 30 sec | homogenous |
| 70% | 30 sec | homogenous |
| 80% | 30 sec | homogenous |

From the results in Table 4, it appears that reconstitution time is slightly decreased in the presence of salt, but was found to be more or less independent of cosolvent composition.

B. Apparent Viscosity

Apparent viscosity measurements made at 25° C. on each sample produced values in the range 7-15 cP and as summarized in Table 5, viscosities were higher overall for formulations with NaCl. Furthermore, the viscosity measurements of formulations with NaCl were not affected by cosolvent composition, however formulations without salt were found to be a function of cosolvent composition and showed a decrease in viscosity with decreasing cosolvent composition.

TABLE 5

Apparent viscosity measurements of reconstituted TBA formulations with and without NaCl.

| TBA | TBA: H2O | SD | TBA: NaCl | SD |
|---|---|---|---|---|
| 80% | 15.1 | 0.67 | 13.1 | 1.8 |
| 70% | 12.6 | 2.15 | 14.6 | 1.1 |
| 60% | 8.3 | 0.30 | 11.3 | 3.5 |

TABLE 5-continued

Apparent viscosity measurements of reconstituted TBA formulations with and without NaCl.

| TBA | TBA: H2O | SD | TBA: NaCl | SD |
|---|---|---|---|---|
| 50% | 7.3 | 0.70 | 12.1 | 4.2 |
| 40% | 9.8 | 1.20 | 14.6 | 1.5 | n = 3 vials, 1 measurement each

C. Surface Activity

Figure 3:
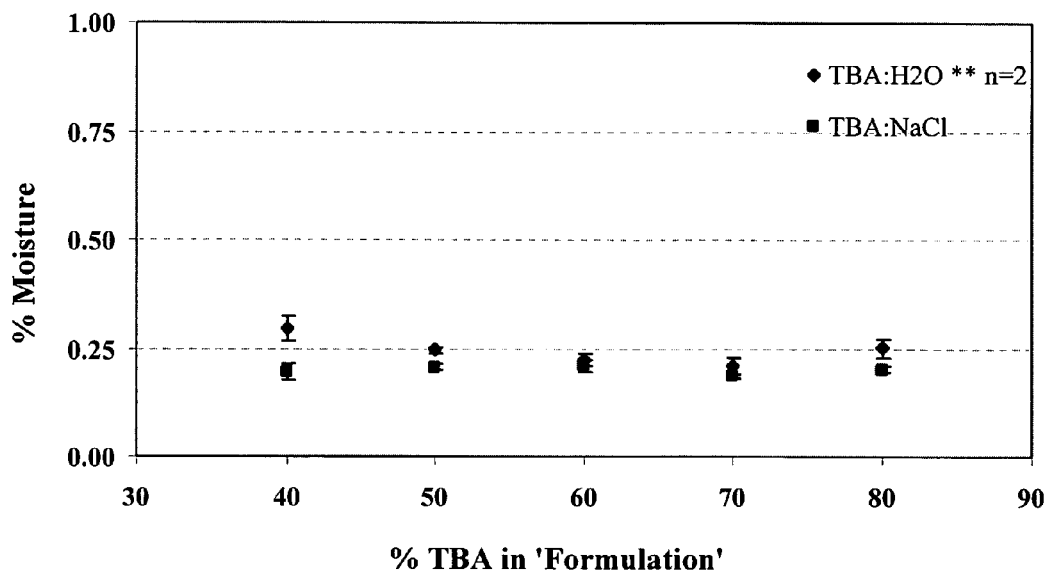
FIG. 3 illustrates the surface activity data for exemplary reconstituted lyophilized KL4 formulations with and without salt. TBA is t-butanol.

The in vitro surface activities of all reconstituted formulations, as measured by PBS at 3 mg-TPL/ml, are shown in FIG. 3. The product release criteria of minimum surface tension is less than or equal to 10 mN/m and the results summarized show that all formulations without salt exhibited low surface activity, with values measured at the different cosolvent compositions being indistinguishable i.e. surface activity was not found to be a function of cosolvent composition. Values measured for formulations with salt were slightly higher and again solvent composition was not seen to adversely affect the measurements made.

Figure 4:
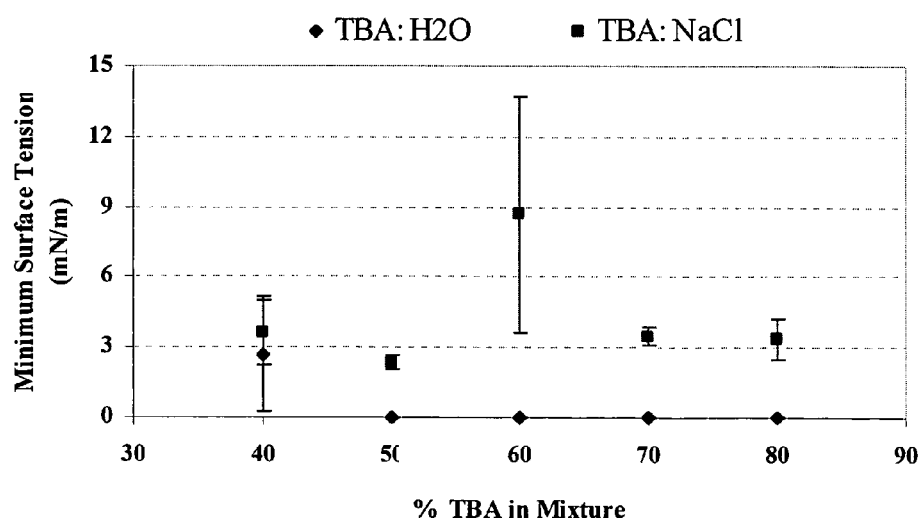
FIG. 4 illustrates the residual moisture data for exemplary lyophilized KL4 formulations with and without salt. TBA is t-butanol.

The measured residual moisture contents for representative vials (averages of three determinations) with and without salt, are presented graphically in FIG. 4. For all samples tested, residual moisture was low, with the average moisture content being 0.2% and was not found to be dependent on either salt content or % TBA in the formulation.

Table 6 summarizes the in vivo activity results for pre-lyophilized formulations containing varying compositions of TBA cosolvent (50, 60 and 70% were tested), with or without salt. All samples were found to readily pass the in vivo assay, defined as average increase in compliance of >150% and p<0.05 relative to the control group. Although the increases in compliance were reported to be some of the strongest observed by the UCSD group conducting the experiments, it must be noted that the assay is/was not designed to compare formulations with each other.

TABLE 6

Summary of in vivo activity results for pre-lyophilized formulations containing varying compositions of TBA cosolvent.

| Description | # Animals (Control) | # Animals (Test) | Ave (Compliance/Wt) (Control) | Ave (Compliance/Wt) (Test) | % Increase | P Value | Result |
|---|---|---|---|---|---|---|---|
| TBA 70% + Nacl | 6 | 6 | 0.059 | 0.402 | 681% | 0.040 | Pass |
| TBA 60% + Nacl | 6 | 6 | 0.059 | 0.292 | 495% | 0.022 | Pass |
| TBA 50% + Nacl | 6 | 6 | 0.068 | 0.386 | 569% | 0.000 | Pass |
| TBA 70% no Nacl | 6 | 6 | 0.068 | 0.271 | 398% | 0.000 | Pass |
| TBA 60% no Nacl | 6 | 6 | 0.068 | 0.395 | 580% | 0.002 | Pass |
| TBA 50% no Nacl | 6 | 6 | 0.063 | 0.344 | 548% | 0.000 | Pass |

The above findings indicate that 60% TBA without NaCl as the optimal cosolvent. Hence, follow-up solubility studies were performed to ensure robustness of the solubility data for both individual components as well as mixed systems. Table 7 summarizes the results of the solubility study.

TABLE 7

Summary of achievable dissolution concentrations for individual components in 60% TBA cosolvent without NaCl.

| | Measured Concentration (mg/ml) | | | | |
|---|---|---|---|---|---|
| Component | 1 | 2 | 3 | AVG | RSD |
| DPPC | 34.8 | 35.0 | 35.2 | 35.0 | 0.7% |
| POPG | 298.4 | 283.7 | 290.6 | 290.9 | 2.5% |
| PA | 43.3 | 42.9 | 41.3 | 42.5 | 2.5% |
| KL4 | 36.0 | 41.9 | 37.6 | 38.5 | 7.9% |

In comparing the solubilities of individual components in 60% TBA (Table 7) with those for the same components in a mixed component system, the solubility of PA can be seen to be significantly affected by, and increased in the presence of, the other components. That is, PA alone has a room temperature solubility of 42.5 mg/ml in 60% TBA where, in mixed component solutions, PA at 10 mg/ml appears to not be fully solubilized.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

All publications and patent documents cited above are hereby incorporated by reference in their entirety for all purposes to the same extent as if each were so individually denoted.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

What is claimed:

1. A method for producing a lyophilized lung surfactant composition having reduced viscosity upon reconstitution as compared to the viscosity of an identical liquid lung surfactant composition which was not lyophilized, the method comprising:

providing a lung surfactant polypeptide having at least 10 amino acid residues and represented by a formula:

$$(Z_a U_b)_c Z_d$$

wherein Z represents a hydrophilic amino acid residue and U represents a hydrophobic amino acid residue; wherein each Z is independently R, D, E or K; and each U is independently V, I, L, C, Y, or F; and wherein a is an integer with an average value of about 1 to about 5; b is an integer with an average value of about 3 to about 20; c is an integer of about 1 to about 10; and d is an integer of about 1 to about 3;

combining the lung surfactant polypeptide, one or more phospholipids, and at least one or more of a fatty acid, a fatty alcohol or a fatty acid ester in an organic solvent system, said system comprising an organic solvent in an amount sufficient to (i) solubilize the lung surfactant polypeptide and lipids to form a substantially homogeneous liquid mixture, and (ii) reduce viscosity of the lyophilized lung surfactant upon reconstitution, wherein the organic solvent system comprises from about 30% by volume to about 70% by volume of the organic solvent with the remainder being aqueous solvent and the organic solvent comprises a lower oxyhydrocarbon; and lyophilizing the substantially homogeneous liquid mixture to obtain the lyophilized lung surfactant composition having reduced viscosity upon reconstitution.

2. The method of claim 1 wherein the substantially homogeneous liquid mixture is filtered before lyophilization.

3. The method of claim 1 wherein the substantially homogeneous liquid mixture is filter sterilized before lyophilization.

4. The method of claim 1 wherein the lung surfactant polypeptide composition is sterilized after lyophilization.

5. The method of claim 1 wherein the lung surfactant polypeptide comprises SEQ ID NO:1 (KL4).

6. The method of claim 1 wherein the one or more phospholipids are selected from the group consisting of dipalmitoyl phosphatidylcholine (DPPC) and palmitoyloleoyl phosphatidylglycerol (POPG), and the fatty acid is palmitic acid.

7. The method of claim 1 wherein the organic solvent system comprises from about 40% by volume to about 60% by volume of organic solvent.

8. The method of claim 7 wherein the organic solvent system comprises about 50% by volume of organic solvent.

9. The method of claim 1 wherein the oxyhydrocarbon is methanol, ethanol, n-propanol, iso-propanol, n-butanol, iso-butanol, 2-butanol, t-butanol, pentanol, iso-pentanol, 2-pentanol, 3-pentanol, t-pentanol, methylethylketone, benzylalcohol, acetic acid, methylethyl ketone, or a combination thereof.

10. The method of claim 1 wherein the oxyhydrocarbon is methanol, ethanol, n-propanol, iso-propanol, n-butanol, iso-butanol, 2-butanol, t-butanol, or a combination thereof.

11. The method of claim 10 wherein the oxyhydrocarbon is t-butanol.

12. A method for producing a reconstituted liquid lung surfactant composition having reduced viscosity upon reconstitution as compared to an identical liquid lung surfactant composition which was not lyophilized, the method comprising:

(a) providing a lung surfactant polypeptide having at least 10 amino acid residues and represented by a formula:

$$(Z_a U_b)_c Z_d$$

wherein Z represents a hydrophilic amino acid residue and U represents a hydrophobic amino acid residue; wherein each Z is independently R, D, E or K; and each U is independently V, I, L, C, Y, or F; and wherein a is an integer with an average value of about 1 to about 5; b is an integer with an average value of about 3 to about 20; c is an integer of about 1 to about 10; and d is an integer of about 1 to about 3;

(b) combining the lung surfactant polypeptide, one or more phospholipids and at least one or more of a fatty acid, a fatty alcohol or a fatty acid ester in an organic solvent system, said system comprising an organic solvent in an amount sufficient to (i) solubilize the lung surfactant polypeptide and lipids to form a substantially homogeneous liquid mixture and (ii) reduce viscosity of the lyophilized lung surfactant upon reconstitution provided that the organic solvent system comprises from about 30% by volume to about 70% by volume of the organic solvent with the remainder being aqueous solvent and the organic solvent comprises a lower oxyhydrocarbon;

(c) lyophilizing the substantially homogeneous liquid mixture to obtain the lyophilized lung surfactant composition; and (d) reconstituting the lyophilized lung surfactant composition with a sufficient amount of a pharmaceutically acceptable dispersing agent to yield a reconstituted liquid lung surfactant composition, wherein the reconstituted liquid lung surfactant composition has reduced viscosity as compared to the viscosity of an identical liquid lung surfactant composition which was not lyophilized.

13. The method of claim 12 wherein the reconstituted liquid lung surfactant composition comprises SEQ. ID. NO: 1 (KL4).

* * * * *

SEQUENCE LISTING

<160> NUMBER OF SEQ ID NOS: 13

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Asp Leu Leu Leu Leu Asp Leu Leu Leu Leu Asp Leu Leu Leu Leu Asp
1               5                   10                  15

Leu Leu Leu Leu Asp
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Arg Leu Leu Leu Leu Arg Leu Leu Leu Leu Arg Leu Leu Leu Leu Arg
1               5                   10                  15

Leu Leu Leu Leu Arg
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

Arg Leu Leu Leu Leu Leu Leu Leu Leu Arg Leu Leu Leu Leu Leu Leu
1               5                   10                  15

Leu Leu Arg Leu Leu
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic Construct

<400> SEQUENCE: 5

Arg Arg Leu Leu Leu Leu Leu Leu Leu Arg Arg Leu Leu Leu Leu Leu

```
            1               5                  10                 15
Leu Leu Arg Arg Leu
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Arg Leu Leu Leu Leu Cys Leu Leu Leu Arg Leu Leu Leu Leu Leu Cys
1               5                  10                 15
Leu Leu Leu Arg
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic Construct

<400> SEQUENCE: 7

Leu Leu Leu Leu Leu Cys Leu Leu Leu Arg Leu Leu Leu Leu Cys Leu
1               5                  10                 15
Leu Leu Arg Leu Leu
            20

<210> SEQ ID NO 8
<211> LENGTH: 49
<212> TYPE: PRT
<213> ORGANISM: Artificial Sequence
<220> FEATURE:
<223> OTHER INFORMATION: Synthetic Construct

<400> SEQUENCE: 8

Arg Leu Leu Leu Leu Cys Leu Leu Leu Arg Leu Leu Leu Leu Cys Leu
1               5                  10                 15
Leu Leu Arg Leu Leu Leu Leu Cys Leu Leu Leu Arg Asp Leu Leu Leu
            20                  25                 30
Asp Leu Leu Leu Asp Leu Leu Leu Asp Leu Leu Leu Asp Leu Leu Leu
                35                  40                 45
Asp

<210> SEQ ID NO 9
<211> LENGTH: 19
<212> TYPE: PRT
<213> ORGANISM: Artificial Sequence
<220> FEATURE:
<223> OTHER INFORMATION: Synthetic Construct

<400> SEQUENCE: 9

Arg Leu Leu Leu Leu Cys Leu Leu Leu Arg Leu Leu Leu Leu Cys Leu
1               5                  10                 15
Leu Leu Arg

<210> SEQ ID NO 10
<211> LENGTH: 21
<212> TYPE: PRT
<213> ORGANISM: Artificial Sequence
<220> FEATURE:
```

```
<223> OTHER INFORMATION: Synthetic Construct

<400> SEQUENCE: 10

Arg Leu Leu Leu Leu Cys Leu Leu Arg Leu Leu Leu Leu Cys Leu
1               5                   10                  15

Leu Leu Arg Leu Leu
            20

<210> SEQ ID NO 11
<211> LENGTH: 28
<212> TYPE: PRT
<213> ORGANISM: Artificial Sequence
<220> FEATURE:
<223> OTHER INFORMATION: Synthetic Construct

<400> SEQUENCE: 11

Arg Leu Leu Leu Leu Cys Leu Leu Arg Leu Leu Leu Leu Cys Leu
1               5                   10                  15

Leu Leu Arg Leu Leu Leu Leu Cys Leu Leu Leu Arg
            20                  25

<210> SEQ ID NO 12
<211> LENGTH: 21
<212> TYPE: PRT
<213> ORGANISM: Artificial Sequence
<220> FEATURE:
<223> OTHER INFORMATION: Synthetic Construct

<400> SEQUENCE: 12

Lys Leu Leu Leu Leu Leu Leu Leu Leu Lys Leu Leu Leu Leu Leu
1               5                   10                  15

Leu Leu Lys Leu Leu
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic Construct

<400> SEQUENCE: 13

Lys Lys Leu Leu Leu Leu Leu Leu Leu Lys Lys Leu Leu Leu Leu Leu
1               5                   10                  15

Leu Leu Lys Lys Leu
            20
```